(12) United States Patent
Krysinski et al.

(10) Patent No.: US 11,819,075 B2
(45) Date of Patent: Nov. 21, 2023

(54) COMPRESSION GARMENT

(71) Applicants: Kimberly Ann Krysinski, Sewickley, PA (US); Terrance Raymond Krysinski, Sewickley, PA (US)

(72) Inventors: Kimberly Ann Krysinski, Sewickley, PA (US); Terrance Raymond Krysinski, Sewickley, PA (US)

(*) Notice: Subject to any disclaimer, the term of this patent is extended or adjusted under 35 U.S.C. 154(b) by 0 days.

(21) Appl. No.: 16/819,146

(22) Filed: Mar. 15, 2020

(65) Prior Publication Data

US 2020/0288797 A1    Sep. 17, 2020

Related U.S. Application Data

(60) Provisional application No. 62/818,874, filed on Mar. 15, 2019.

(51) Int. Cl.
A41D 31/04 (2019.01)
A61F 13/08 (2006.01)
A41D 1/08 (2018.01)

(52) U.S. Cl.
CPC .............. *A41D 31/04* (2019.02); *A41D 1/08* (2013.01); *A61F 13/08* (2013.01); *A41D 2400/32* (2013.01)

(58) Field of Classification Search
CPC ........ A41D 31/04; A41D 31/08; A41D 31/18; A41D 2400/32; A41D 13/1254; A41D 13/0506; A41D 31/02; A41D 31/00; A41D 31/0005; A41D 2500/10; A41D 2500/20; A41D 2500/30; A41D 17/02; A61F 13/08; A41B 11/14; D04B 9/46; D04B 9/52

USPC ............................................................. 2/79
See application file for complete search history.

(56) References Cited

U.S. PATENT DOCUMENTS

| 3,953,895 A | * | 5/1976 | Lowth | A61F 13/08 2/409 |
| 4,527,402 A | * | 7/1985 | Swallow | D04B 37/02 66/232 |
| 5,097,537 A | * | 3/1992 | Ewing | A41B 11/003 2/241 |
| 2006/0085895 A1 | * | 4/2006 | Wojeski | A41B 11/14 2/409 |
| 2009/0113596 A1 | * | 5/2009 | Young | A41D 1/00 602/61 |
| 2010/0130903 A1 | * | 5/2010 | Rock | D04B 1/243 602/62 |
| 2011/0000005 A1 | * | 1/2011 | Brown | A61F 5/0111 2/243.1 |

(Continued)

*Primary Examiner* — Bao-Thieu L Nguyen
*Assistant Examiner* — Uyen T Nguyen
(74) *Attorney, Agent, or Firm* — Dentons Cohen & Grigsby P.C.

(57) ABSTRACT

A compression garment may generally include an upwardly disposed waist, a seat spaced apart from and connected to a pant front, the seat and the pant front connected to the waist, a single leg portion connected to the seat and the pant front and configured to receive a first leg of a wearer, and an opposing side portion connected to the seat and the pant front and including an aperture opposed to the waist and defined by distal edges of the seat and the pant front, and a compression portion circumferentially around at least a portion of the first leg of the wearer to exert therapeutic pressure on the first leg of the wearer when the compression garment is in use.

14 Claims, 3 Drawing Sheets

(56) References Cited

U.S. PATENT DOCUMENTS

| | | | |
|---|---|---|---|
| 2011/0016602 A1* | 1/2011 | Berns | A41D 13/0015 |
| | | | 703/2 |
| 2011/0224639 A1* | 9/2011 | Venable | A61F 13/496 |
| | | | 604/385.01 |
| 2012/0172940 A1* | 7/2012 | Wahls | A61N 1/0476 |
| | | | 607/3 |
| 2018/0049482 A1* | 2/2018 | Erkus | A41D 1/06 |
| 2019/0133871 A1* | 5/2019 | Chase | A41D 13/0015 |

* cited by examiner

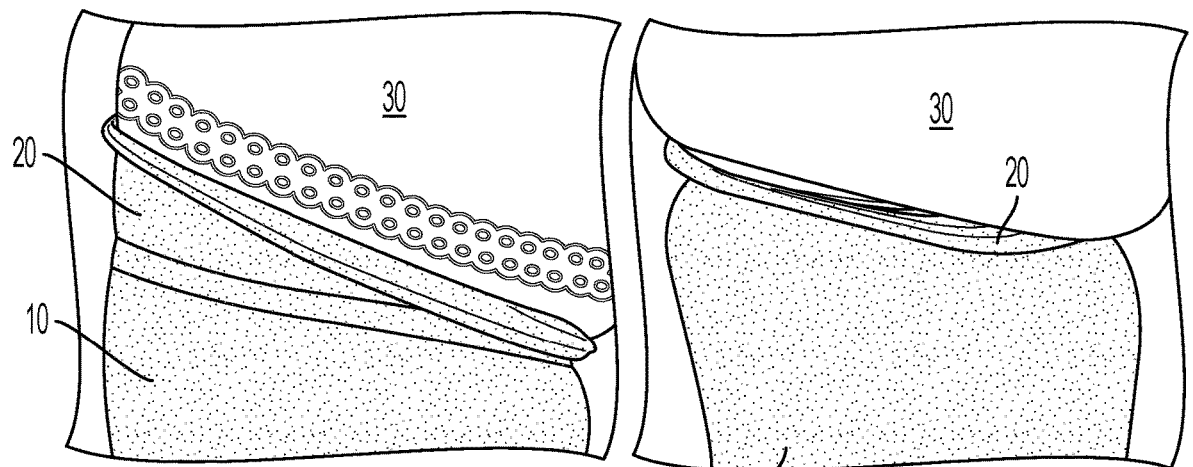
FIG. 1
PRIOR ART
FIG. 2
PRIOR ART
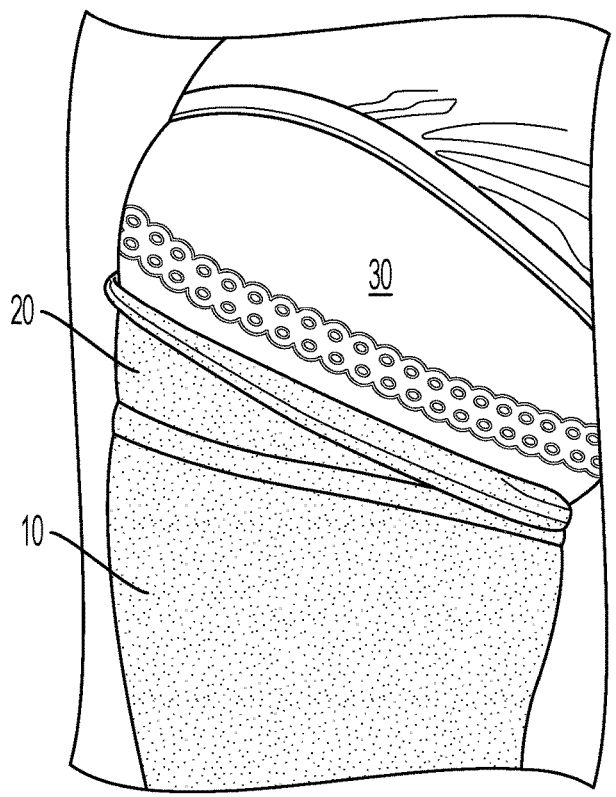
FIG. 3
PRIOR ART

COMPRESSION GARMENT

CROSS REFERENCE TO RELATED APPLICATION

This application claims priority to U.S. provisional application Ser. No. 62/818,874, filed on Mar. 15, 2019, which is incorporated herein by reference in its entirety.

FIELD OF INVENTION

The present invention generally relates to compression garments that may be useful for medical and therapeutic applications.

BACKGROUND

Compression garments are articles of clothing that provide compressive pressure to regions of a wearer's body. Compression garments for therapeutic and medical applications may be used for treating edema, poor blood circulation, lymphedema, thrombosis or other venous and lymphatic system dysfunctions. Examples of compression garments for therapeutic and medical applications include pants, pantyhose, stockings, socks, and sleeves. Compression stockings, for example, may circumferentially surround the wearer's legs to promote circulation of blood and lymph fluid and direct blood and lymph fluid away from the legs and towards the wearer's torso. As a result of their compressive properties, compression garments may be difficult for a wearer to put on and take off. Accordingly, more efficient and/or cost-effective compression garments may be desirable.

DESCRIPTION OF THE DRAWINGS

The present invention described herein may be better understood by reference to the accompanying figures, in which:

FIGS. 1-3 show a conventional compression garment.

DETAILED DESCRIPTION

Figure 4:
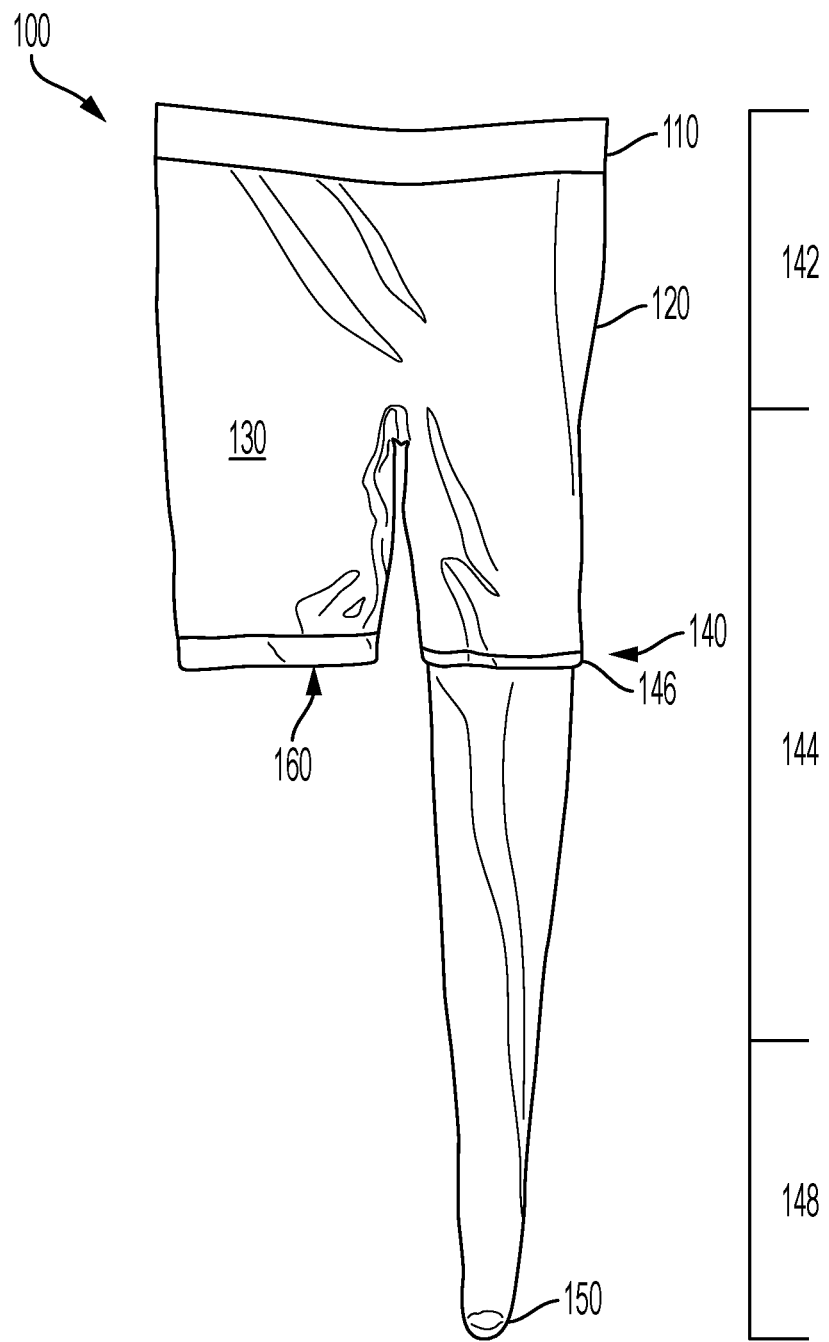
FIGS. 4 and 5 show a compression garment according to the present invention.

All numerical quantities stated herein are approximate, unless indicated otherwise, and are to be understood as being prefaced and modified in all instances by the term "about". The numerical quantities disclosed herein are to be understood as not being strictly limited to the exact numerical values recited. Instead, unless indicated otherwise, each numerical value included in this disclosure is intended to mean both the recited value and a functionally equivalent range surrounding that value.

All numerical ranges recited herein include all sub-ranges subsumed therein. For example, a range of "1 to 10" and "1-10" is intended to include all sub-ranges between (and including) the recited minimum value of 1 and the recited maximum value of 10, that is, having a minimum value equal to or greater than 1 and a maximum value equal to or less than 10.

As generally used herein, the articles "one", "a", "an", and "the" include "at least one" or "one or more" of what is claimed or described, unless indicated otherwise. For example, "a component" means one or more components, and thus, possibly, more than one component is contemplated and may be employed or used in an implementation of the described embodiments.

As generally used herein, the terms "include", "includes", and "including" are meant to be non-limiting.

As generally used herein, the terms "have", "has", and "having" are meant to be non-limiting.

As generally used herein, the term "characterized by" is meant to be non-limiting.

Compression garments for therapeutic and medical applications may have varying levels of compression or pressure. For example, Class 1 compression garments (less than 15 mmHg, 10-20 mmHg, 15-20 mmHg) may provide relief from minor edema, Class 2 compression garments (15-30 mmHg, 20-30 mmHg) may provide relief from moderate varicose veins, lipedema and lymphedema, Class 3 compression garments (20-40 mmHg, 30-40 mmHg) may provide relief from sever lymphedema, lipedema and deep venous thrombosis, and Class 4 compression garments (>30 mmHg, >40 mmHg, >50 mmHg, 30-50 mmHg, 40-50 mmHg, 50-60 mmHg) may provide relief for high pressure applications. Consultation with a medical professional may be required for Class 2 and higher compression garments.

As a result of their compressive properties, conventional compression garments may be difficult for a wearer to put on and take off. Conventional compression garments include knee high and pantyhose style garments, which may include a silicone band at the top of the garment, thigh high style garments, which may include a stirrup, and pantyhose. Conventional compression garments may be pulled along the wearer's limbs transversely to the direction of the garment's pressure when putting on or taking off these garments. This may be difficult when the wearer is fitted in a high-pressure garment (e.g., at least Class 3), when the wearer has limited arm or hand strength, or when the wearer has limited mobility. Medical professionals may suggest various tips to wear these garments, such as putting it on immediately in the morning before a shower or bath, turning the garment inside-out and easing it up the limb one bit at a time, applying talcum powder to the limb, and avoiding applying moisturizers to the skin until the nighttime. While donning aids such as rubber gloves, stocking donners, lotions, and the like may provide some assistance, such aids may have to be purchased separately and may be relatively expensive and/or difficult to use.

Referring to FIGS. 1-3, unlike non-compressive garments, many important considerations may be taken into account in the manufacture and use of compression garments. Compression garments may be required to be fitted to the wearer; if they are too loose, they may not control swelling, and if they are too tight, they may restrict blood flow. Inaccurate measurements or poorly manufactured compression garments may cause severe pain and/or discomfort to the wearer. The class of compressive garment also determines its method of manufacture, e.g., circular knitted garments may be manufactured in one piece using a fixed number of needles and without a seam, and therefore, may be only recommended for mild to moderate edema. In contrast, flat-bed knitted garments may be manufactured in multiple pieces joined together with a seam and therefore may be recommended for moderate to severe edema.

Further, when worn for a long period of time, wearers of compression garments should not fold over the top of the compression garment or turn back the hand-piece or foot of the compression garment because this may increase the compression in a small area in a circumferential way which may worsen the swelling. Wearers should also ensure that the compression garment is free from wrinkles, creases, or folds because these may damage the skin underneath the compression garment or cause a tourniquet effect that may worsen the swelling.

In the case of wearers of lower body compression garments, the ability of these wearers to use the restroom may also be an important issue. Wearers of compression garments may wear it for several hours a day, weeks, months, or years at a time, even for the rest of their lives. Due to the aforementioned difficulty in putting on and taking off these garments, compression garment manufacturers may provide a fixed opening cut near the genital area for the purpose of passing waste while remaining in the compression garment. For example, for women, the garment may comprise a opening near the gusset. Yet, requiring sole usage of the waste removal opening may be undesirable because the compression garment may be soiled by waste that does not sufficiently clear the opening. Moreover, access to the opening for cleaning may be limited when seated because the compression applied by the garment may force the legs towards each other.

To address these issues, medical professionals may recommend people wear thigh high or knee high compression stockings as they do not require removal prior to restroom usage. However, conventional garments with silicon bands along the upper thigh may roll causing areas of constriction. For example, these garments may have a tendency for slipping, wrinkling, or gathering of material, e.g., often around knee and ankle areas, unless a silicone grip top band or adhesive is used. As shown in FIGS. 1 and 3, conventional compression garments 10 may include a silicon grip top band 20 that may slip and roll down causing irritation to and marking of the skin 30. As shown in FIG. 2, constriction of the skin 30 and leg as a result of the compression may occur above the silicone grip top band 20. Yet another disadvantage of a conventional thigh high compression garment may be that compression is only applied for the length of the garment. For example, when a wearer only pulls up the compression stocking to mid-thigh, the area above that may not receive the benefit of the compression garment.

The present invention is generally directed to more efficient and/or cost-effective compression garments useful for medical and therapeutic applications.

When the garment is applied on the limb, the extension of the limb defines the following directions: the circumference of the limb defines circumferential directions of the garment. The long extension of the limb defines axial directions of the garment. Radial directions of the garment are directions orthogonal to the axial directions.

The garment may be elongate, i.e. it has an elongated shape and extends lengthwise in axial directions. An elongate garment may comprise a plurality of axial sections.

The garment, elongate or not, may comprise one or more of a waist section for application around the waist, a front section for application around the front area between the waist and hips, a seat section for application around the rear between the waist and hips, a thigh section for application around the thigh, and/or a calf section for application around at least a portion of the calf, and/or a foot section for application around at least a portion of the foot. The foot section, in turn, may comprise a heel section for application around at least a portion of the heel, an optional middle section for application around at least a portion of the metatarsus, and an optional toe section for application around at least a portion of the toes. The foot section may include an optional ankle section for application around at least a portion of the ankle. Each section of the garment may be independently adapted to provide therapeutic compression or other functions, but no compression.

The garment may be a compression stocking. The stocking may comprise a sleeve further comprising a foot section. The foot section may comprise at least a heel section, and may further comprise a middle section and/or an optional toe section.

The garment may provide therapeutic compression from the properties of the materials of which the garment is made. The garment may comprise elastic strands and/or non-elastic strands. The non-elastic strands may provide certain desired mechanical properties to the garment. The non-elastic strands comprise strands that cannot be elongated, e.g. in axial directions. non-elastic strands may help stabilize the garment. Suitably arranged in circumferential directions, non-elastic strands may provide an "abutment" against excessive circumferential elongation of the garment. The elastic strands may comprise a mixture of polyurethane strands and polyurea strands, polyether strands, polyester strands, poly(meth)acrylate strands, polyolefin strands, or polyvinyl chloride strands. The entire garment or portions thereof may comprise the elastic strands and/or non-elastic strands. Portions of the garment may comprise only elastic strands and be free of non-elastic strands. Portions of the garment may be free of elastic strands. Portions of the garment may comprise both elastic strands and non-elastic strands. A good balance is achieved if the therapeutic pressure on the limb remains above a level of 0 mmHg, greater than 5 mm Hg, at least 15 mmHg, such as between 15-40 mm Hg, after an extended period (e.g. 5, 10, or 15 minutes) of no movement of the wearer, while the compression garment may still be put on easily by the wearer.

The compression section of the garment may be arranged in different locations in the garment. In one aspect, the compression section may be arranged such as to exert therapeutic pressure on the calf, when the compression garment is in use. The compression garment may comprise a compression stocking, or may be comprised in a compression stocking, and the compression section may be arranged to exert therapeutic pressure on the calf, when the compression stocking is in use. In other aspects, the compression garment may comprise a compression stocking, or may be comprised in a compression stocking, and the compression section may be arranged to exert therapeutic pressure on the thigh, or on both the calf and the thigh, when the compression stocking is in use.

Applying a compression garment on a patient's limb is sometimes referred to as "donning", and removal is sometimes referred to as "doffing". Certain traditional compression garment may be hard to don, because they must provide a considerable elastic force in order to compress the limb effectively after application. Before donning, the patient or a caregiver may have to open the garment wide enough, against the elastic force, for the limb to slip in. Similarly, when removing a traditional garment, it may have to be opened to some degree, against the elastic force, in order to reduce friction between the skin and the garment and to be able to remove the garment from the limb. A garment according to the present disclosure is generally easier to don relative to such traditional compression garments.

Compression garments according to the present invention may comprise lower body compression garments extending to the waist, such as compression pantyhose, leggings, tights, pants, trousers, shorts, and the like. Compression garments according to the present invention may reduce or prevent the above issues because the compression garment is supported by the body above the groin and up to the waist.

Due to the difficulty of putting on or taking off conventional compression garments, wearers may find compression garments according to the present invention more desirable.

The present invention may provide wearers the ease of a thigh high when using the bathroom. As well as the additional benefit of the fit of a pantyhose by having the wearer's body from the groin to the waist support the compression garment to reduce the amount or prevent the use of a top grip silicon band and all its adverse components as well as limiting migration of the garment down the wearer's leg.

Referring to FIG. 4, the compression garment 100 may comprise an upwardly disposed waist 110, a seat 120 spaced apart from and connected to a pant front 130, the seat and the pant front connected to the waist, a single leg portion 140 having Class 1 or greater gradient compression from the foot 150 to the waist 110 connected to the seat 120 and the pant front 130 configured to receive a first leg of a wearer, and an aperture 160 configured to receive a second leg of the wearer having an elastic non gradient compression of 5-10 mmHg from mid-thigh to groin. The aperture 160 may be opposed to the waist 110 and defined by distal edges of the seat 120 and the pant front 130. The single leg portion 140 may comprise one or more of an upper leg portion (proximal end) 142, a lower leg portion (intermediate portion) 144, and a foot portion (distal end) 148. The single leg portion 140 may exert a compressive pressure against the wearer's leg. The lower leg portion 144 may extend from the foot portion 148 upward to a knee area 146 of the wearer. The upper leg portion 142 may extend from the seat 120 and the pant front 130 downward to the knee area 146 of the wearer. The foot portion 148 may comprise one of an open end and a closed end 150, such as a closed heel and an open or closed toe, for example. The foot portion 148 may comprise a stirrup to engage the wearer's foot when the foot portion comprises an open end.

The garment may be configured to be worn on either leg of the wearer. As shown in FIG. 4, the garment may be worn on the wearer's left leg. The present invention may allow for compression of a single leg with no or less rolling of the garment along the wearer's upper thigh. The present invention may comprise non-compression underwear and a shortened leg section to provide easier pull down for going to the bathroom. The garment may comprise an opening in the front panel for men or crotch area for women to allow the wearer to not have to remove the garment to go to the bathroom. The compression garment may more easily facilitate the donning and removal process relative to conventional compression garments because only the single leg portion extends from the waist to the foot portion. When donning the garment, a wearer first places the leg needing compression into the single leg compression portion and pulls up the garment along the leg until the top of the garment is aligned with the groin or the waist. The wearer then places the other leg into and through the short leg aperture once both legs are in their perspective apertures the compression garment may be pulled up to the waist. When the wearer subsequently wants to take off the garment, the wearer simply has to pull the garment down from the waist. The wearer may more easily remove the garment by removing the shorter leg from the aperture followed by removing the leg needing compression from the single leg portion. A method of using a compression garment may be as substantially described in the specification and accompanying drawing.

The single leg portion (i.e., the short side or long side) may be characterized by at least one circumferential zone having a compressive force to exert compressive pressure against the wearer's leg. The at least one circumferential zone may extend circumferentially and wholly encompass or surround an associated body region of the wearer, such as the thigh, knee, ankle or foot. The single leg portion may comprise a plurality of circumferential zones each having different compression forces. The long side may be configured to provide full leg compression, and the short side may be configured to provide stabilization. The long side may provide medical grade compression of Class 1 and above, exerting gradient compression from the foot up to the groin. The short side may have an elastic compression of 5-10 mmHg from mid-thigh to the waist.

The foot portion or lower leg portion may comprise a first zone to exert the greatest pressure in the foot and/or ankle area (distal end) and the upper leg portion may comprise a second zone exerting less pressure in the knee or thigh area (proximal end) than the first zone. The levels of compression may provide a gradual increase in compression along a length of the leg portion with less compression in the knee and/or thigh area (proximal end) and increasingly higher compression in foot and/or ankle area (distal end). This arrangement may help to improve blood circulation from the ankle upward, minimize leg fatigue, reduce the risk of blood clotting and/or enhance the comfort level of the wearer. Each zone may similarly have a gradient of pressure that generally increases from the proximal end to the distal end.

The waist, seat, and/or pant front may comprise easy stretch fabrics having a first level of compression (e.g., having a compression pressure of 5-30 or 5-10 mmHg) and constructed to minimize restriction of movement. The upper leg portion and/or lower leg portion may comprise a tight fitting fabric having a second level of compression (e.g., having a compression pressure of 20-50 mmHg) that is different from and relatively greater than the first level of compression. The lower leg portion and/or foot portion may comprise compression fabrics having a third level of compression (e.g., having a compression pressure of 40-80 mmHg or 40-50 mmHg) that is different from and relatively greater than the second level of compression. The garment may provide 20 mmHg of compression at the ankle, 10 mmHg of compression at the knee, and essentially 0 mmHg at the waist or hips. The garment may provide 20-30 mmHg of compression at the ankle, 10-15 mmHg of compression at the knee, and essentially 0-5 mmHg at the waist or hips. The garment may provide 30-40 mmHg of compression at the ankle, 10-20 mmHg of compression at the knee, and 0-10 mmHg at the waist or hips. Some compression gradients described herein may require or benefit from prescription guidance from a medical professional.

The compression gradient of the garment may be substantially linear in its variance, as in the examples provided herein, but may vary in non-linear fashions as well, for example with high compression at the ankle, equally or nearly as equally high compression at the knee, rapidly decreasing compression over the thighs, and then nearly no compression at the waist. The number of zones may vary as desired and may be customized for a particular individual based on physical characteristics and/or medical condition.

The compression garment may comprise any suitable yarn or fiber. Examples of suitable yarn or fibers may include synthetic yarn or fibers, e.g., of polyester, nylon, or acrylic; natural yarn or fibers formed, e.g., of cotton or wool; and regenerate yarn or fibers, such as rayon, and combinations thereof. The different levels of compression in the easy stretch, tight fitting, and compression portions of the garment may be achieved by using different elastomeric yarns (e.g., yarns with differing mechanical stretch), such as Spandex and Lycra, different elastomeric yarn count, different denier elastomeric yarn, and/or different wt. % elastomeric yarn. For example, the easy stretch portion may include 0.5-10 wt. %, e.g., 4.5 wt. %, elastomeric yarn; the tight fitting portion may include 4-20 wt. % elastomeric yarn, e.g., 8 wt. %, elastomeric yarn; and the compression portion may include 8-35 wt. %, e.g., about 13.5 wt. %, elastomeric yarn.

The garment may be knitted on a conventional knitting machine. For example, a pattern of circumferential zones of differing compression may be knitted on a circular knitting machine to form a single layer fabric body. A plurality of single layer fabric bodies may be assembled (e.g., during a cut-and-sew process) to form a compression garment to cover all or substantial portions of a wearer's leg. Each circumferential zone may comprise one or more regions of differential compression seamlessly interconnected with each other to minimize or avoid the cut-and-sew process. The circumferential zones may extend entirely circumferentially with no seam along the circumference. The garment may be formed with seamless construction along its length such that each zone is seamlessly interconnected with another. Minimizing the number of seams in the garment may help to contribute to overall comfort and wearability.

Figure 5:
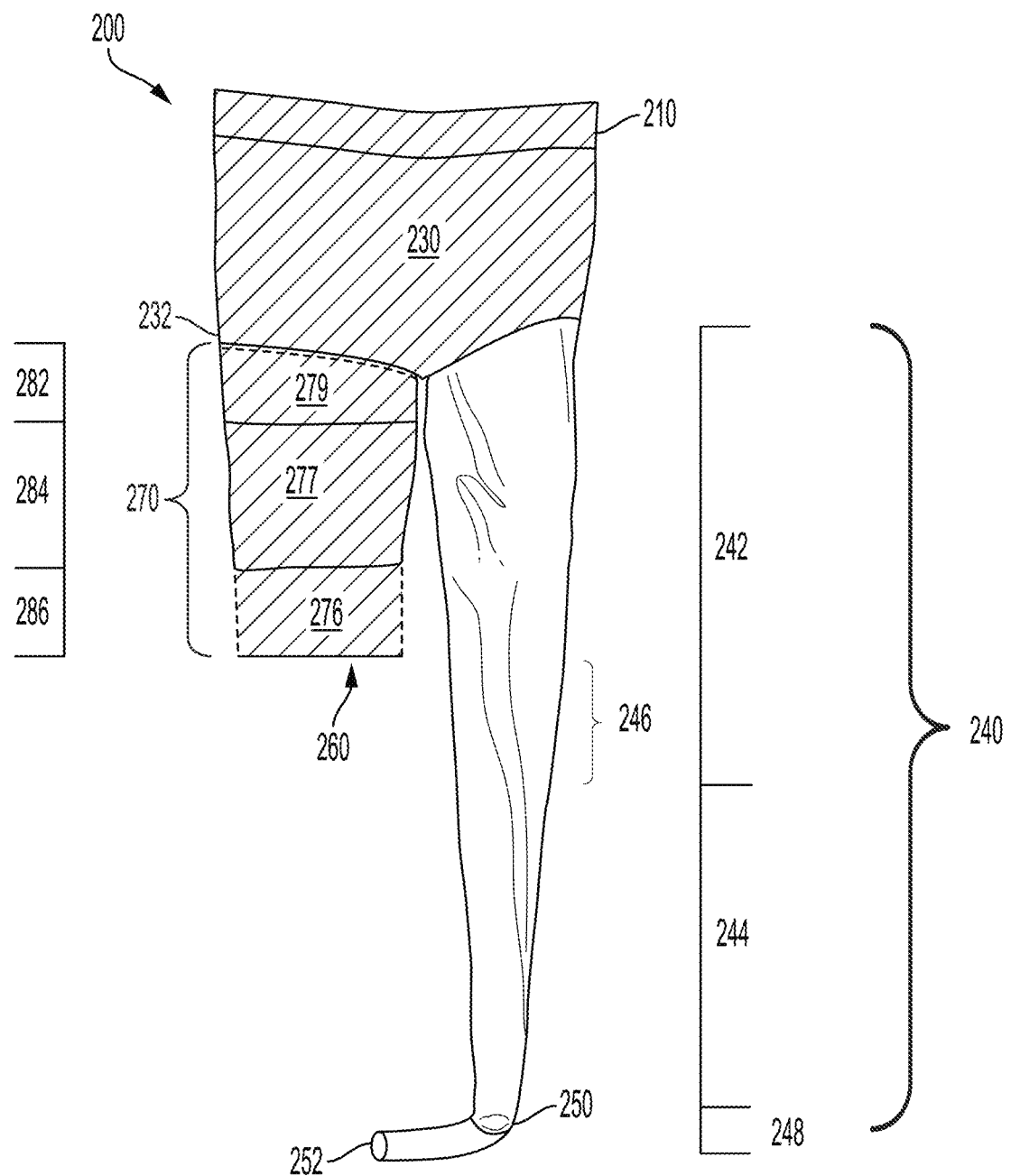

Referring to FIG. 5, the compression garment 200 may comprise an upwardly disposed waist 210, a seat 220 spaced apart from and connected to a pant front 230, the seat 220 and the pant front 230 connected to the waist 210, a therapeutic compression portion 240 and a support portion 270. The seat 220 and the pant front 230 may independently comprise compression from 0-15 mmHg. The therapeutic compression portion 240 and support portion 270 may be each connected to the seat 220 and the pant front 230 proximate to the inguinal line 232. The therapeutic compression portion 240 may be configured to receive a first leg of a wearer. The support compression portion 270 may comprise an aperture 260 configured to receive a second leg of the wearer.

The support compression portion 270 may comprise length defined by the distance from the waist 210 to the aperture 260. The length may be to the inguinal line 232 or the length may extend beyond the inguinal line 232. For example, the length may be to the inguinal line 232, the length may be a short length 282 extending 2-3 inches beyond the inguinal line 232 such that the support compression portion 270 comprises portion 279, a medium length 284 extending 6-8 inches beyond the inguinal line 232 to the mid-thigh area of the wearer such that the support compression portion 270 comprises portions 277, 279, or a long length 286 extending 10-12 inches beyond the inguinal line 232 to the distal-thigh area of the wearer such that the support compression portion 270 comprises portions 276, 277, 279. The support compression portion 270 may comprise compression from 0-15 mmHg. The support portion may comprise gradient compression from 0-15 mmHg when the length extends beyond the inguinal line. For example, the short length 282 may comprise 0-5 mmHg, the medium length 284 may comprise 5-10 mmHg, and the long length 286 may comprise 10-15 mmHg.

Referring to FIG. 5, the therapeutic compression portion 240 may provide gradient compression from the foot area 250 up to the inguinal crease (groin line) 232 proximate to the sapheno-femoral junction of the venous system. The therapeutic compression portion 240 may extend beyond the inguinal line 232. The therapeutic compression portion 240 may comprise an upper portion extending beyond the inguinal line 232 to the knee area 246. The upper portion may comprise a short length extending 2-3 inches beyond the inguinal line 232, a medium length extending 6-8 inches beyond the inguinal line 232 to the mid-thigh area of the wearer, or a long length extending 10-12 inches beyond the inguinal line 232 to the distal-thigh area of the wearer. The therapeutic compression portion 240 may comprise a lower portion extending from the knee area 246 of the wearer. The lower portion may extend to the foot area 250 of the wearer. The therapeutic compression portion 240 may provide gradient compression from the foot 250 to the groin comprising medical grade compression of Classes I, II, III, and IV. For example, the compression of the foot area may be independently selected 30 mmHg, 40 mmHg, or 50 mmHg, and the compression of the groin area may be independently selected from 20 mmHg, 30 mmHg, or 40 mmHg.

Referring to FIG. 5, the therapeutic compression portion 240 may comprise one or more of an upper leg portion (proximal end) 242, a lower leg portion (intermediate portion) 244, and a foot portion (distal end) 248. The single leg portion 240 may exert a compressive pressure against the wearer's leg. The lower leg portion 244 may extend from the foot 250 or the foot portion 248 upward to a knee area 246 of the wearer. The upper leg portion 242 may extend from the seat 220 and the pant front 230 downward to the knee area 246 of the wearer. The foot portion 248 may comprise one of an open end and a closed end 252, such as a closed heel and an open or closed toe, for example. The foot portion 248 may comprise a stirrup to engage the wearer's foot when the foot portion comprises an open end.

A method for making a garment according to the present invention may generally comprise determining the desired compression gradient along the garment, determining the compressive force desired at each zone along the garment relative to the anatomical portion of a wearer and/or medical condition of the wearer, selecting a base textile in view of the desired compression and compression gradient desired and the compressive force provided by the base textile, selecting the amount of elastomer or other compressive material required to achieve the desired amount of compression at each zone along the garment, and forming the garment from the textile, by stitching, gluing, or any other process. The garment may be made using a cut-and-sew process to achieve the gradual compression. For example, individual fabric segments may be cut into predefined shapes and then assembled together (e.g., by stitching along seams) in a predetermined pattern via a sewing process to achieve the desired compression.

Examples

The present invention may be better understood when read in conjunction with the following representative example. The following example is included for purposes of illustration and not limitation.

Referring to FIG. 4, a compression garment according to the present invention may comprise a plurality of circumferential zones of differing compression knitted on a circular knitting machine. The garment may comprise a high compression zone comprising the greatest compression (about 30-50 mmHg) at the foot/ankle; optionally, a tight fitting zone comprising an intermediate compression (about 20-40 mmHg) intermediate the foot/ankle and waist; and an easy stretch zone comprising the lowest compression (about 0-25 mmHg) configured as underwear or a short anchor leg component. The garment may be dyed. The leg portion may be coupled to the seat and the pant front (e.g., by stitching) to form a compression garment. The garment may comprise only one leg portion such that it may be easier to put on than a conventional two legged compression garment, and therefore, may be more comfortable for the wearer. The wearer may use an ordinary stocking generally matching the weave of the leg portion of the garment on the other leg.

Referring to FIG. 5, a compression garment according to the present invention may comprise a plurality of circumferential zones of differing compression knitted on a circular knitting machine. The garment may comprise a high compression zone comprising the greatest compression (about 30-50 mmHg) at the foot/ankle; optionally, a tight fitting zone comprising an intermediate compression (about 20-40 mmHg) 244 intermediate the foot/ankle and waist; and an easy stretch zone comprising the lowest compression (about 0-20 mmHg) configured as underwear or a short anchor leg component. The garment may be dyed. The leg portion may be coupled to the seat and the pant front (e.g., by stitching) to form a compression garment. The garment may comprise only one leg portion such that it may be easier to put on than a conventional two legged compression garment, and therefore, may be more comfortable for the wearer. The wearer may use an ordinary stocking generally matching the weave of the leg portion of the garment on the other leg.

The following aspects are disclosed in the present invention:

Aspect 1. A compression garment comprising: an upwardly disposed waist, a seat spaced apart from and connected to a pant front, the seat and the pant front connected to the waist, a single leg portion connected to the seat and the pant front and configured to receive a first leg of a wearer, and an opposing side portion connected to the seat and the pant front and comprising an aperture opposed to the waist and defined by distal edges of the seat and the pant front; and a compression portion circumferentially around at least a portion of the first leg of the wearer to exert therapeutic pressure on the first leg of the wearer when the compression garment is in use.

Aspect 2. The garment of Aspect 1, wherein the garment is configured to not exert therapeutic pressure on a second leg of the wearer when the compression garment is in use.

Aspect 3. The garment of Aspects 1 or 2, wherein the single leg portion comprises the compression portion, and the opposing side portion comprises a stabilization portion.

Aspect 4. The garment of any of the forgoing Aspects, wherein the single leg portion comprises: an upper leg portion extending from the seat and the pant front downward to a knee area of the wearer, a lower leg portion extending from a foot area of the wearer upward to the knee area of the wearer, and a foot portion extending from an ankle area of the wearer downward to a toe area of the wearer, wherein the single leg portion comprises the compression portion having a plurality of circumferential zones each having a different compression force.

Aspect 5. The garment of any of the forgoing Aspects, wherein the compression portion comprises: an upper circumferential zone comprising the upper leg portion having a compression force from 0-10 mmHg; an intermediate circumferential zone comprising the lower leg portion having a compression force from 10-20 mmHg; and a lower circumferential zone comprising the foot portion having a compression force 30-40 mmHg.

Aspect 6. The garment of any of the forgoing Aspects, wherein the upper circumferential zone comprises the seat and the pant front having a compression force from 0-5 mmHg.

Aspect 7. The garment of any of the forgoing Aspects, wherein the lower circumferential zone comprises circumferentially and wholly encompasses the wearer's ankle and foot.

Aspect 8. The garment of any of the forgoing Aspects, wherein the lower circumferential zone does not circumferentially and wholly encompasses the wearer's foot.

Aspect 9. The garment of any of the forgoing Aspects, wherein the compression portion comprises: the waist comprises a compression force from 0-10 mmHg; the knee area of the wearer having a compression force from 10-15 mmHg; the ankle area of the wearer having a compression force from 20-30 mmHg; and the toe area of the wearer having a compression force 30-40 mmHg.

Aspect 10. The garment of any of the forgoing Aspects, wherein the opposing side portion comprises a compression force less than the compression force of the compression portion.

Aspect 11. The garment of any of the forgoing Aspects, wherein the opposing side portion comprises a stabilization force from 0-15 mmHg.

Aspect 12. The garment of any of the forgoing Aspects, wherein the compression portion comprises a non-linear compression portion comprising the seat and the pant front having a compression force from 0-5 mmHg; the knee area of the wearer having a compression force from 10-30 mmHg; the ankle area of the wearer having a compression force from 20-40 mmHg; and the toe area of the wearer having a compression force 0-2 mmHg.

Aspect 13. The garment of any of the forgoing Aspects, wherein stabilization portion circumferentially and wholly encompasses the second leg of the wearer to exert stabilization pressure on the second leg of the wearer when the compression garment is in use, wherein the stabilization pressure is less than the therapeutic pressure.

Aspect 14. The garment of any of the forgoing Aspects, wherein the stabilization portion comprises: the waist, the knee area of the wearer, the ankle area of the wearer, the toe area of the wearer, wherein the stabilization portion comprises a stabilization pressure from 0-15 mmHg.

Aspect 15. The garment of any of the forgoing Aspects, wherein the stabilization portion has a length less than a length of the compression portion.

Aspect 16. The garment of any of the forgoing Aspects, wherein the compression portion comprises: the waist comprises a compression force from 0-20 mmHg; the thigh area of wearer having a compression force 20-40 mmHg; the knee area of the wearer having a compression force from 20-40 mmHg; the ankle area of the wearer having a compression force from 20-50 mmHg; the toe area of the wearer having a compression force 30-50 mmHg; and the stabilization portion comprises: the waist comprises a compression force from 0-20 mmHg; and lacks the knee area, ankle area, and toe area of the wearer.

Aspect 17. The garment of any of the forgoing Aspects, wherein the compression portion comprises: the waist comprises a compression force from 0-15 mmHg; the knee area of the wearer having a compression force from 10-30 mmHg; the ankle area of the wearer having a compression force from 20-50 mmHg; the toe area of the wearer having a compression force 30-50 mmHg; and the stabilization portion comprises: the waist comprises a compression force from 0-15 mmHg; the knee area of the wearer having a compression force from 0-15 mmHg; and lacks the ankle area and the toe area of the wearer.

Aspect 18. The garment of any of the forgoing Aspects, wherein the compression portion comprises: the waist comprises a compression force from 0-15 mmHg; the knee area of the wearer having a compression force from 10-30 mmHg; the ankle area of the wearer having a compression force from 20-40 mmHg; the toe area of the wearer having a compression force 30-40 mmHg; and the stabilization portion comprises: the waist comprises a compression force from 0-15 mmHg; the knee area of the wearer having a compression force from 0-15 mmHg; the ankle area of the wearer having a compression force from 0-15 mmHg; and lacks the toe area of the wearer.

Aspect 19. The garment of any of the forgoing Aspects comprising a fastening system comprising a first attachment element fastened to the single leg portion and a second attachment element fastened to the waist, which releasably fastens to the first attachment element.

Aspect 20. The garment of any of the forgoing Aspects comprising one of a knitted fabric, a woven fabric, and a non-woven fabric.

All documents cited herein are incorporated herein by reference, but only to the extent that the incorporated material does not conflict with existing definitions, statements, or other documents set forth herein. To the extent that any meaning or definition of a term in this document conflicts with any meaning or definition of the same term in a document incorporated by reference, the meaning or definition assigned to that term in this document shall govern. The citation of any document is not to be construed as an admission that it is prior art with respect to this application.

While particular embodiments have been illustrated and described, it would be obvious to those skilled in the art that various other changes and modifications can be made without departing from the spirit and scope of the invention. Those skilled in the art will recognize, or be able to ascertain using no more than routine experimentation, numerous equivalents to the specific apparatuses and methods described herein, including alternatives, variants, additions, deletions, modifications and substitutions. This application including the appended claims is therefore intended to cover all such changes and modifications that are within the scope of this application.

What is claimed is:

1. A compression garment comprising:
    an upwardly disposed waist;
    a seat spaced apart from and connected to a pant front, the seat and the pant front connected to the waist;
    a therapeutic compression portion connected to the seat and the pant front proximate to an inguinal line and configured to receive a first leg of a wearer, wherein the therapeutic compression portion comprises an upper leg portion extending from the inguinal line downward to a knee area of the therapeutic compression portion, a lower leg portion extending from a foot area of the therapeutic compression portion upward to the knee area of the therapeutic compression portion, and a foot portion extending from an ankle area of the therapeutic compression portion downward to a toe area of the therapeutic compression portion; and
    a support portion connected to the seat and the pant front proximate to the inguinal line configured to receive a second leg of a wearer;
    wherein the support portion in combination with the seat, pant front, and the waist is configured to prevent rolling of the therapeutic compression portion along the first leg of the wearer when the compression garment is in use;
    wherein the support portion comprises a length different than a length of the therapeutic compression portion;
    wherein the therapeutic compression portion is configured to circumferentially exert therapeutic pressure on at least a portion of the first leg of the wearer when the compression garment is in use;
    wherein the therapeutic pressure of the therapeutic compression portion is at least 15 mmHg;
    wherein the support portion is configured to exert a pressure different than the therapeutic pressure of the therapeutic compression portion on the second leg of the wearer when the compression garment is in use; and
    wherein the waist, the seat, the pant front, and the support portion consist of a single layer fabric body.

2. The garment of claim 1, wherein the support portion extends beyond the inguinal line by at least one length selected from 2-3 inches, 6-8 inches, and 10-12 inches.

3. The garment of claim 1, wherein the support portion lacks a knee area portion, an ankle area portion, and a toe area portion.

4. The garment of claim 1, wherein the support portion comprises a compression force greater than zero and less than a compression force of the therapeutic compression portion.

5. The garment of claim 1, wherein the support portion comprises a compression force less than the therapeutic pressure of the therapeutic compression portion.

6. The garment of claim 1, wherein the support portion comprises a stabilization force greater than zero and less than 15 mmHg.

7. The garment of claim 1, wherein the seat and the pant front have a compression force greater than zero and less than 15 mmHg.

8. The garment of claim 1, wherein the therapeutic compression portion comprises a non-linear compression force.

9. The garment of claim 1, wherein the therapeutic compression portion-comprises a plurality of circumferential zones each having a different compression force.

10. The garment of claim 9, wherein the plurality of circumferential zones of the therapeutic compression portion comprises:
    an upper circumferential zone comprising the upper leg portion having a compression force from 20-40 mmHg;
    an intermediate circumferential zone comprising the lower leg portion having a compression force from 20-40 mmHg; and
    a lower circumferential zone comprising the foot portion having a compression force from 20-40 mmHg;
    wherein the compression force of the lower circumferential zone is greater than the compression force of the intermediate circumferential zone; and
    wherein the compression force of the intermediate circumferential zone is greater than the compression force of the upper circumferential zone.

11. The garment of claim 9, wherein the lower circumferential zone is configured to circumferentially and wholly encompass the wearer's ankle and foot.

12. The garment of claim 9, wherein the lower circumferential zone is configured to not circumferentially and wholly encompass the wearer's foot.

13. A compression garment comprising:
    an upwardly disposed waist;
    a seat spaced apart from and connected to a pant front, the seat and the pant front connected to the waist;
    a therapeutic compression portion connected to the seat and the pant font proximate to an inguinal line and configured to receive a first leg of a wearer, wherein the therapeutic compression portion comprises an upper leg portion extending from the inguinal line downward to a knee area of the therapeutic compression portion, a lower leg portion extending from a foot area of the therapeutic compression portion upward to the knee area of the therapeutic compression portion and a foot portion extending from an ankle area of the therapeutic compression portion downward to a toe area of the therapeutic compression portion; and a support portion connected to the seat and the pant front proximate to the inguinal line and configured to receive a second leg of a wearer;

wherein the therapeutic compression portion is configured to circumferentially exert a gradient of therapeutic pressure on at least a portion of the first leg of the wearer that increases from the upper leg portion of the therapeutic compression portion to the foot portion of the therapeutic compression portion when the compression garment is in use;

wherein the support portion comprises a length different than a length of the therapeutic compression portion;

wherein the support portion is configured to exert a pressure less than the therapeutic pressure of the therapeutic compression portion when the compression garment is in use;

wherein the therapeutic pressure of the therapeutic compression portion is at least 15 mmHg; and wherein the waist, the seat, the pant front, and the support portion consist of a single layer fabric body.

14. A compression garment comprising:

an upwardly disposed waist;

a seat spaced apart from and connected to a pant front and configured to wholly encompass a thigh area comprising a front thigh area between the waist and an inguinal line at the distal edge of the pant front of a support portion and a rear thigh area between the waist and the inguinal line at the distal edge of the seat of the support portion, the seat and the pant front connected to the waist; and a therapeutic compression portion connected to the seat and the pant front proximate to the inguinal line and configured to receive a first leg of a wearer, wherein the therapeutic compression portion comprises an upper leg portion extending from the inguinal line downward to a knee area of the therapeutic compression portion, a lower leg portion extending from a foot area of the therapeutic compression portion upward to the knee area of the therapeutic compression portion and a foot portion extending from an ankle area of the therapeutic compression portion downward to a toe area of the therapeutic compression portion;

wherein the support portion connected to the seat and the pant front configured to receive a second leg of a wearer;

wherein the support portion extends beyond the inguinal line by 10-12 inches configured to prevent rolling of the therapeutic compression portion along the first leg of the wearer when the compression garment is in use;

wherein the therapeutic compression portion is configured to circumferentially exert therapeutic pressure of at least 15 mmHg on at least a portion of the first leg of the wearer when the compression garment is in use;

wherein the support portion is configured to exert a pressure less than the therapeutic pressure of the therapeutic compression portion on the second leg of the wearer when the compression garment is in use;

wherein the therapeutic compression portion comprises a plurality of circumferential zones each having a different compression force;

wherein the plurality of circumferential zones of the therapeutic compression portion comprises: an upper circumferential zone comprising the upper leg portion having a compression force from 20-40 mmHg; an intermediate circumferential zone comprising the lower leg portion having a compression force from 20-40 mmHg; and a lower circumferential zone comprising the foot portion having a compression force from 20-40 mmHg; wherein the compression force of the lower circumferential zone is greater than the compression force of the intermediate circumferential zone; wherein the compression force of the intermediate circumferential zone is greater than the compression force of the upper circumferential zone; and wherein the waist, the seat, the pant front, and the support portion consist of a single layer fabric body.

* * * * *